United States Patent
Bruder

(10) Patent No.: US 6,925,140 B2
(45) Date of Patent: Aug. 2, 2005

(54) METHOD FOR CORRECTING STRAY RADIATION IN AN X-RAY COMPUTED TOMOGRAPHY SCANNER

(75) Inventor: Herbert Bruder, Höchstadt (DE)

(73) Assignee: Siemens Aktiengesellschaft, Münich (DE)

( * ) Notice: Subject to any disclaimer, the term of this patent is extended or adjusted under 35 U.S.C. 154(b) by 186 days.

(21) Appl. No.: 10/169,972

(22) PCT Filed: Nov. 6, 2001

(86) PCT No.: PCT/DE01/04147

§ 371 (c)(1),
(2), (4) Date: Nov. 4, 2002

(87) PCT Pub. No.: WO02/39790

PCT Pub. Date: May 16, 2002

(65) Prior Publication Data

US 2003/0138074 A1 Jul. 24, 2003

(30) Foreign Application Priority Data

Nov. 10, 2000 (DE) .................................... 100 55 739

(51) Int. Cl.⁷ ................................................ G21K 1/12
(52) U.S. Cl. ................................ 378/4; 378/7; 378/19
(58) Field of Search ........................... 378/4, 5, 7, 19, 378/62, 70, 86, 87, 901

(56) References Cited

U.S. PATENT DOCUMENTS

| 4,644,575 A | | 2/1987 | Kruger et al. ............ 378/98.8 |
|---|---|---|---|
| 4,727,562 A | | 2/1988 | Belanger ................. 378/98.8 |
| 4,995,107 A | | 2/1991 | Klingenbeck .............. 378/7 |
| 5,270,925 A | * | 12/1993 | Stegehuis ................ 378/7 |
| 5,533,088 A | * | 7/1996 | Fivez .................... 378/98.4 |
| 5,615,279 A | * | 3/1997 | Yoshioka et al. ......... 382/131 |
| 5,771,269 A | * | 6/1998 | Chao .................... 378/5 |
| 6,041,097 A | | 3/2000 | Roos et al. .............. 378/62 |
| 6,687,326 B1 | * | 2/2004 | Bechwati et al. ......... 378/7 |

FOREIGN PATENT DOCUMENTS

| EP | 0 698 047 | 12/1995 |
|---|---|---|
| GB | 1 476450 | 6/1977 |
| GB | 1 551 669 | 8/1979 |

* cited by examiner

Primary Examiner—Edward J. Glick
Assistant Examiner—Courtney Thomas
(74) Attorney, Agent, or Firm—Schiff Hardin LLP

(57) ABSTRACT

In a method for correcting for stray radiation in measured intensity values, the measured intensity values are obtained in an X-ray computed tomography scanner by means of a detector matrix that is situated in a tomography measuring field of the computer tomography scanner and has a multiplicity of detector elements arranged next to one another in a number of adjacent detector rows. At least one reference distribution of the stray radiation intensity is determined in the row direction of the detector matrix, and a stray radiation component of each measured value of intensity is determined starting from this at least one reference distribution, and the measured intensity values are corrected as a function of their respective stray radiation component. In this case, the stray radiation component of the measured values of intensity of at least a fraction of the detector rows is determined by using a recursion method on the basis of the reference distribution.

35 Claims, 1 Drawing Sheet

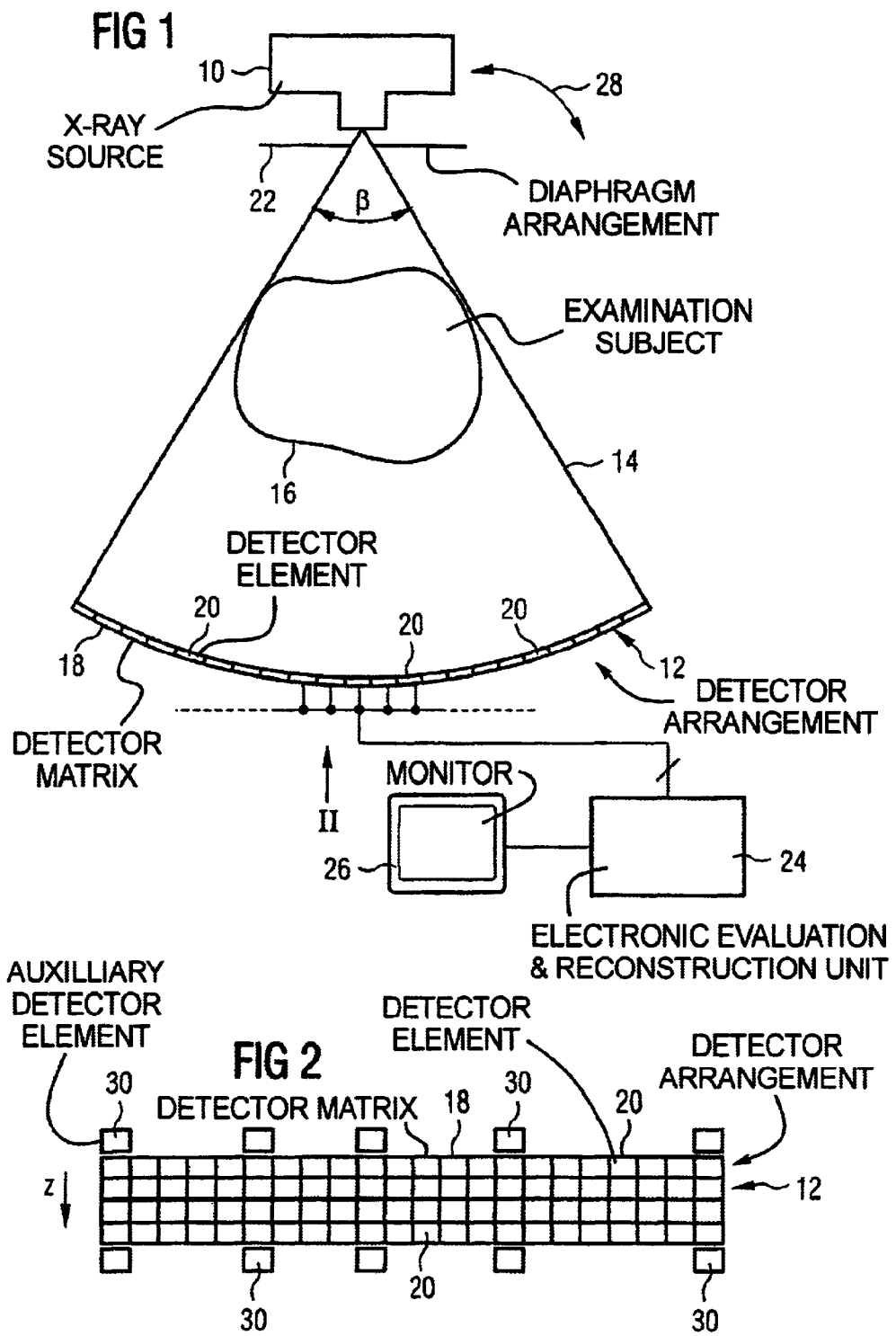

METHOD FOR CORRECTING STRAY RADIATION IN AN X-RAY COMPUTED TOMOGRAPHY SCANNER

BACKGROUND OF THE INVENTION

1. Field of the Invention

The present invention relates to the correction of image artifacts in X-ray computed tomography that are caused by stray radiation.

2. Description of the Prior Art

Just like beam hardening effects scattering effects can cause undesired image artifacts in the reconstructed tomographic image of a transirradiated layer of a patient or some other object under examination. These image artifacts simulate structures corresponding to no real anatomy of the object under examination, and therefore lead to misinterpretations of the tomographic image. Particularly in the medical sector, such misinterpretations can have grave consequences to the extent of endangering the life of the patient.

In order to suppress the stray radiation component in the radiation intensity values measured with a detector, it is known to collimate at the detector side the X-ray radiation transirradiating the object under examination. As a rule, collimators are produced from tungsten, which is very well suited for this because of its high attenuation. However, tungsten has the disadvantage of being very expensive. This cost disadvantage is particularly significant when the detector is a detector matrix with a multiplicity of detector elements arranged next to one another in a number of superimposed detector rows. In the case of such detectors, the depth of the collimator shaft provided for each individual detector element must be enlarged with an increasing number of rows. The outlay for design and materials would be viewed as no longer acceptable starting from a certain number of detector rows.

SUMMARY OF THE INVENTION

It is an object of the present invention to avoid with a lesser outlay image artifacts caused by stray radiation in the case of multirow detectors.

This object is achieved in a method for correcting stray radiation for measured values of radiation intensity that are obtained in an X-ray computed tomography scanner by means of a detector matrix that is situated in a tomography measuring field of the scanner and has a multiplicity of detector elements arranged next to one another in a number of adjacent detector rows.

In accordance with the invention at least one reference distribution of the stray radiation intensity is determined in the row direction of the detector matrix, and then a stray radiation component of each measured intensity value is determined starting from this reference distribution, and the measured intensity values are corrected as a function of their respective stray radiation component. The stray radiation component of the measured intensity values of at least a fraction of the detector rows are determined by recursion in the following way:

a) the stray radiation component of the measured intensity values of a current detector row of the recursion is determined from the measured intensity values of this current detector row and a primary radiation component of the measured intensity values of a preceding detector row of the recursion, b) the primary radiation component of the measured intensity values of the preceding detector row is determined from the measured intensity values of this preceding detector row and the stray radiation component thereof, and c) intensity values from the reference distribution of the stray radiation intensity are used as stray radiation component of the measured intensity values of a first detector row of the recursion.

As used herein primary radiation means that radiation component of the total radiation incident on the detector elements that reaches the detector matrix without being scattered, that is to say on a direct path from the radiation source of the computer tomography scanner. A tomography measuring field means a measuring zone fitted with detector elements in which the measured total radiation includes a primary radiation component. As a rule, the tomography measuring field is fixed by a diaphragm arrangement at the source side.

In the solution according to the invention, the stray radiation component is estimated by calculation for all detector rows with using at least one reference distribution. Expensive collimator shafts thus can be dispensed with. The recursion, which is applied at least for a fraction of the detector rows, offers the basis for taking account of a profile of the stray radiation component that changes across the span of the detector rows.

In a first refinement of the method according to the invention, the at least one reference distribution of the stray radiation intensity is obtained from measured values of the reference intensity that are obtained by measuring radiation intensity outside the tomography measuring field. The fact that no primary radiation occurs outside the tomography measured field is thereby utilized. Measuring elements arranged there consequently detect only stray radiation. It is easily possible to determine a distribution of the stray radiation in the row direction, which is then used as the reference distribution.

The radiation intensity will expediently be measured above a first detector row of the detector matrix or/and below a last detector row of the detector matrix.

In general, the spatial profile of the stray radiation can be represented by a comparatively low-frequency function. It is therefore sufficient to record measured values for the stray radiation in the row direction only in a relatively coarse array. In other words, the measured values of reference intensity are preferably obtained at measuring points that are situated at a mutual spacing in the row direction of the detector matrix and of which the number is smaller, in particular much smaller than the number of the detector elements per detector row. The reference distribution of the stray radiation intensity then can be easily obtained by interpolation of the measured values of reference intensity.

It is even possible to obtain one reference distribution by measuring the radiation intensity above the first detector row of the detector matrix, and a further reference distribution by radiation intensity measurement below the last detector row of the detector matrix.

The recursion preferably should be begun at least in a detector row on the edge of the detector matrix. The assumption that the stray radiation intensity outside the tomography measuring field differs—if at all—only insubstantially from the stray radiation intensity in a detector row at the edge will apply here, as a rule. Consequently, the error that arises when intensity values from the reference distribution are used as stray radiation component of the measured values of intensity from the detector row at the edge will be negligible.

In a second refinement of the method according to the invention, the at least one reference distribution of the stray radiation intensity is calculated by using the measured intensity values of at least one detector row of the detector matrix. In particular, it is possible in this case for the reference distribution to be calculated on the basis of a mathematical convolutional model. Such a convolutional model is known, for example, for a computed tomography scanner with detector elements arranged in a single row from B. Ohnesorge: "Untersuchungen der Scatter-Korrektur in Elektronenstrahl-Computertomographen Chair of Information Technology of the University of Erlangen-Nuremberg, Dissertation 1994. By adapting this convolutional model to a multirow detector matrix, it is possible to estimate the stray radiation distribution for a detector row of the matrix by calculation from the measured intensity values obtained for this detector row.

It could be noted that the stray radiation distribution could fundamentally be calculated in each case in all detector rows with the aid of the above convolutional model, and that a recursion would then be superfluous. However, convolutional operations can be very demanding computationally. The application of recursion for at least a fraction of the detector rows renders it possible, by contrast, to keep the computational outlay within acceptable limits and, at the same time, to take account of possible changes in the stray radiation distribution from detector row to detector row.

The reference distribution will expediently be calculated by using the measured intensity values of a middle detector row of the detector matrix, and the recursion will be begun toward upper and lower detector rows at least in this middle detector row. It goes without saying, however, that the reference distribution can also be calculated with the aid of the measured values of intensity of another detector row, in particular even of a detector row at the edge.

In order to improve the quality of the results obtained for the stray radiation component of the measured intensity values, the recursion can be ended after a fraction of detector rows, and a further recursion can be started in a subsequent detector row. The further recursion can be started in this case on the basis of the same or another reference distribution of the stray radiation intensity.

If the object under examination includes comparatively contrasting structures, the measured intensity values can change relatively strongly from detector row to detector row and/or within a detector row from detector element to detector element. This is due to a rapid change in the stray radiation (which—as already mentioned—changes only comparatively slowly in space, as a rule) but is due to spatially changing attenuation properties of the transirradiated material. So that such instabilities in the measured total intensity do not substantially falsify the stray radiation components, which are used in the final analysis to correct the measured values of intensity, the stray radiation components determined after carrying out the recursion preferably are subjected to low pass filtering in the column direction and, if desired, also in the row direction of the detector matrix. The low pass filtering filters out from the recursively determined stray radiation components those changes of intensity, which have a comparatively high spatial frequency. These are usually a result of changes in the attenuation properties. The filtered stray radiation components thus reproduce the low frequency profile of the stray radiation very well. The measured intensity values are then corrected as a function of their respective filtered stray radiation component.

A refinement of the estimate obtained for the stray radiation component of the measured intensity values is possible when starting from two different reference distributions, two values of the stray radiation component are determined for each measured intensity values, and the measured intensity values are corrected in accordance with a respective averaged stray radiation component.

Independently of the recursive determination of the stray radiation component, the inventive method includes determining the reference distribution by means of measuring the radiation intensity outside the tomography measuring field. According to a second aspect, the invention therefore further provides a method for correcting stray radiation for measured values of radiation intensity that are obtained in an X-ray computed tomography scanner by means of a detector matrix that is situated in a tomography measuring field of the computed tomography scanner and has a multiplicity of detector elements arranged next to one another in a number of adjacent detector rows. In this case according to the invention that at least one reference distribution of the stray radiation intensity in the row direction of the detector matrix is obtained from measured values of reference intensity that are obtained by measuring radiation intensity outside the tomography measuring field, and that a stray radiation component of each measured intensity value is then determined starting from this at least one reference distribution, and the measured intensity values are corrected as a function of their respective stray radiation component.

In order to estimate the stray radiation component of the measured intensity values, it is also possible to apply the recursion, explained earlier, with the steps a) to c). However, it is also conceivable to use an intensity value from the reference distribution of the stray radiation intensity as the stray radiation component. In this case, the reference distribution is simply taken over directly as stray radiation distribution for each detector row. In cases where the stray radiation intensity actually changes only slightly over the span of the detector matrix, it is possible already to achieve very good results. If, by contrast, marked changes in the stray radiation intensity must be dealt with, preference will be given to the recursive mode of procedure.

Of course the method according to the second aspect can be configured by means of further features of the method according to the first aspect.

Additionally the invention is directed to an X-ray computed tomography scanner, which is designed for carrying out the method according to the first or/and second aspect. In particular, in the computed tomography scanner it is possible to provide an auxiliary detector arrangement, arranged outside the tomography measuring field, for obtaining the measured values of reference intensity. Above a first detector row of the detector matrix or/and below a last detector row of the detector matrix the auxiliary detector arrangement can have a number of auxiliary detector elements that are arranged at mutual spacings in the row direction of the detector matrix and of which each supplies one of the measured values of reference intensity. The number of the auxiliary detector elements in the row direction of the detector matrix is in this case preferably smaller, in particular substantially smaller, than the number of the detector elements per detector row.

DESCRIPTION OF THE DRAWINGS

FIG. 1 is a block diagram of an embodiment of a CT scanner according to the invention with a multirow detector matrix.

FIG. 2 is a schematic plan view of the detector matrix as seen in the direction of the arrow II in FIG. 1.

DESCRIPTION OF THE PREFERRED EMBODIMENTS

The CT scanner shown in the figures has an X-ray source 10 and a detector arrangement 12. The X-ray source 10 emits X-ray radiation in the shape of a fan, as indicated at 14. An object under examination 16 arranged in the beam path between the X-ray source 10 and the detector arrangement 12 is penetrated by the X-ray radiation. The detector arrangement 12 detects the X-ray radiation downstream of the object under examination 16. Specifically, the detector arrangement 12 has a detector matrix 18 composed of a multiplicity of detector elements 20 that are distributed over a number of adjacent rows and are arranged next to one another in each row in the direction of a fan angle β. Four such detector rows are shown as an example in FIG. 2; however, the number of the detector rows can differ therefrom as desired and can be 8, 16 or 24, instead, for example. The size of the beam fan 14 in the direction of the fan angle β can be set by means of a diaphragm arrangement 22 that is arranged between the X-ray source 10 and the object under examination 16. The radiation emitted by the X-ray source 10 is likewise bounded by a comparable diaphragm arrangement (not shown) in the column direction of the detector matrix 18, that is to say in a direction z in FIG. 2. In the region of the detector arrangement 12, the diaphragm arrangement 22 and the z-diaphragm arrangement just addressed define a tomography measuring field within which it is possible to detect the primary radiation that strikes the detector arrangement 12 on a straight path from the X-ray source 10 without being scattered in the object under examination 16. The detector matrix 18 is situated completely within this tomography measuring field. Each position in the direction of the fan angle β at which a detector element 20 is located corresponds to a projection channel.

Each detector element 20 detects the radiation incident in its zone of space and supplies a corresponding intensity measuring signal $I_G(n, k)$ to an electronic evaluation and reconstruction unit 24. Here, the index n stands for the number of the row of the detector matrix 18 in which the relevant detector element 20 is located, while k represents the channel number. The evaluation and reconstruction unit 24 firstly carries out a stray radiation correction on the incoming intensity measuring signals $I_G(n, k)$ by subtracting a stray radiation component $I_S(n, k)$ from the intensity measuring signals $I_G(n, k)$. This leaves a primary radiation component $I_P(n, k)$ that is representative of the intensity of the primary radiation incident on the respective detector element 20. The evaluation and reconstruction unit 24 then determines attenuation values from the intensity values $I_P(n, k)$ that it uses to reconstruct a tomographic image, displayed on a monitor 26, of the transirradiated layer of the object under examination 16. The CT scanner requires projections from a multiplicity of different directions in order to reconstruct the tomographic image. The X-ray source 10 can be moved for this purpose in the direction of the arrow 28 around the object under examination 16.

In order to be able to carry out the stray radiation correction, the CT scanner is designed to start by determining a reference distribution of the stray radiation intensity in the row direction. This reference distribution specifies, for each channel k, a reference value $I_{Sref}(k)$ for the stray radiation intensity. In order to determine the reference distribution, the detector arrangement 12 has in addition to the detector matrix 18, a number of auxiliary detector elements 30 (see FIG. 2). These are situated outside the tomography measuring field and therefore are not struck by primary radiation but exclusively by stray radiation. The auxiliary detector elements 30 consequently permit measured information to be obtained on the intensity of the stray radiation. The auxiliary detector elements 30 are also connected to the evaluation and reconstruction unit 24 and supply their measuring signals to the same.

The auxiliary detector elements 30 are arranged above the uppermost row in the z-direction, and/or below the lowermost row in the z-direction, of the detector matrix 18. Since the spatial distribution of the stray radiation can be described in general by a comparatively low frequency function, a coarse array of the auxiliary detector elements 30 suffices in the row direction, and so by comparison with the number of detector elements 20 present per row only a substantially smaller number, for example smaller by an order of magnitude, of auxiliary detector elements 30 is preferably provided in the row direction. The evaluation and reconstruction unit 24 then uses interpolation to determine the reference distribution $I_{Sref}(k)$ supplied by the auxiliary detector elements 30. The auxiliary detector elements 30 are expediently distributed at uniform spacings in the row direction; this is not, however, mandatory. Of course, it is not excluded to provide a number of auxiliary detector elements 30 in the row direction that is equal to the number of the detector elements 20.

In channel k (k=1, ..., N) for the total intensity $I_G(n, k)$ measured in the detector row n (n=1, ..., L):

$$I_G(n, k) = I_P(n, k) + I_S(n, k) \tag{1}$$

The aim of the stray radiation correction carried out in the evaluation and reconstruction unit 24 is firstly to estimate the stray radiation component $I_S(n, k)$ as accurately as possible in order subsequently to have available values for the primary radiation component $I_P(n, k)$ that are as accurate as possible and can be fed to the image reconstruction.

Estimation of the stray radiation begins in the uppermost or the lowermost detector row depending on whether the reference distribution $I_{Sref}(k)$ was obtained from the measuring signals of auxiliary detector elements 30 situated above or below the detector matrix 18. It is assumed below that the operation begins in the uppermost detector row. The channel number is no longer specified explicitly in this case, in order to simplify the notation. The following considerations apply, however, for any desired angular positions in the beam fan, and thus for any desired channel numbers. For the uppermost detector row:

$$I_G(1) = I_P(1) + I_S(1) \tag{2}$$

It is assumed for the purpose of determining the primary radiation intensity $I_P(1)$ in the uppermost (first) detector row that $I_{Sref}$ and the stray radiation component $I_S(1)$ of the first detector row differ from one another—if at all—only negligibly. The primary radiation intensity $I_P(1)$ therefore can be calculated in a simple way as follows:

$$I_P(1) = I_G(1) - I_{Sref} \tag{3}$$

The primary radiation intensities in all further detector rows can now be determined similarly by assuming that the primary radiation intensity $I_P(n-1)$ of the n−1th detector row corresponds approximately to the primary radiation intensity $I_P(n)$ of the nth row. With this assumption, the stray radiation intensity $I_S(n)$ in the nth row can be calculated recursively as follows from the actually measured total intensity $I_G(n)$ in this row and the primary radiation intensity $I_P(n-1)$ in the preceding row n−1:

$$I_S(n) = I_G(n) - I_P(n-1) \tag{4}$$

The primary radiation intensity $I_P(n)$ of the nth row then can be estimated in accordance with:

$$I_P(n) = I_G(n) - I_S(n) \tag{5}$$

The assumption $I_P(n-1)=I_P(n)$ is justified in general in the case of low-contrast structures. If, however, the object under investigation 16 includes contrasting structures such as bone, for example, significant changes can occur in the measured total intensity between consecutive rows and/or channels. The estimated values $I_S(n)$ of the stray radiation intensity are subjected to low pass filtering of selectable length, for example with a median filter. This means that signal instabilities upon transition from row n−1 to row n in the above recursion are not carried over to the calculation of the stray radiation intensities and therefore falsify the $I_P(n)$ values. The low pass filtering removes the instabilities discussed above. The filtered $I_S(n)$ values then reflect a very good estimate of the actual stray radiation intensity. Subsequently, new $I_P(n)$ values that are used for image reconstruction are calculated from the filtered $I_S(n)$ values by substitution in the above equation (5).

The low pass filtering can be carried out as one-dimensional filtering in the z-direction, or else as two-dimensional filtering in the z- and row directions.

If auxiliary detector elements 30 are provided above and below the detector matrix 18, two reference distributions $I_{Sref}1$ and $I_{Sref}2$ can be determined, specifically one $(I_{Sref}1)$ from the measuring signals of the auxiliary detector elements 30 situated above the detector matrix 18, and the other $(I_{Sref}2)$ from the measuring signals of the auxiliary detector elements 30 situated below the detector matrix 18. The above method for recursive estimation of the primary radiation intensities can then be carried out twice, specifically once beginning in the uppermost detector row on the basis of the reference distribution $I_{Sref}1$, and once beginning in the lowermost detector row on the basis of the reference distribution $I_{Sref}2$. Thus, two values $I_P1$ and $I_P2$ of the primary radiation intensity that are subsequently averaged are obtained for each detector element 20. The averaged intensity values are then used for the image reconstruction.

In some instances, it can already suffice to use the reference distribution $I_{Sref}$ obtained with the aid of the auxiliary detector elements 30 as a model for the stray radiation distribution of all the detector rows of the detector matrix 18. The primary radiation intensities $I_P(n)$ can then easily be calculated as follows:

$$I_P(n)=I_G(n)-I_{Sref} \qquad (6)$$

It is also conceivable not to continue the recursion of all the detector rows, but to truncate it after a fraction of the detector rows, for example, after each second, third or fourth detector row or after half of the detector rows, and then to start a new recursion in a new detector row. In this new detector row, the assumption is made again, in a way similar to equation (3), that the stray radiation distribution of this row corresponds to the reference distribution $I_{Sref}$. It is even possible to conceive of proceeding from a different reference distribution upon restarting the recursion. In the above example with auxiliary detector elements 30 above and below the detector matrix, it could be sensible, for example, to carry out a recursion for the upper half of the detector rows on the basis of the reference distribution $I_{Sref}1$ and to carry out a recursion on the basis of the reference distribution $I_{Sref}2$ for the lower half of the detector rows, in particular when the detector matrix 18 has a large number of rows, for example 16, 24 or 32.

The reference distribution $I_{Sref}$ can also be determined in another way than with the aid of the auxiliary detector elements 30. Thus, for example, it is possible to compute the associated stray radiation distribution $I_S(n)$ of a row of the detector matrix 18 from the measured values of intensity $I_G(n)$ of said row. This stray radiation distribution $I_S(n)$ can then be used as reference distribution $I_{Sref}$ in order to estimate for the remaining rows of the detector matrix 18 the stray radiation component of the measured values of intensity of these rows by means of the above recursion method.

A convolutional model for a single-row detector system is known from the literature, cited above, of B. Ohnesorge for the purpose of computing a stray radiation distribution from measured values of intensity. This model is based on the idea, in principle, that the functional dependences of the scattering angle on the differential active cross sections and scattering energies of Compton and Raleigh scattering justify the assumption that the scattering contributions in a detector channel k that belongs to a fan angle $\beta_k$ decrease with the angular spacing in the fan $(\beta-\beta_k)$. (Only simple scattering processes are taken into account in the derivation.) A "spacing function" $G(\beta)$ that can be used for the description then has a maximum at $\beta=\beta_k$ and sweeps over the angular range $(-\beta_{max}+\beta_k, \beta_{max}+\beta_k)$. A stray radiation distribution $I_{SC}(\beta)$ dependent on the fan angle $\beta$ is then yielded as follows:

$$I_{SC}(\beta)=C_M \cdot f(\Delta z_{sl}) \cdot (I_{SC,forw}(\beta) \otimes G(\beta)) \cdot R(\beta) \qquad (7)$$

Here, $C_M$ denotes a machine constant and $f(\Delta z_{sl})$ a weighting dependent on layer thickness. $I_{SC,forw}(\beta)$ is a forward stray radiation intensity, calculated in the model of single scattering, with:

$$I_{SC,forw}(\beta\beta = K_{SC,forw} \cdot I\left(\beta\left(\cdot(-\ln)\left(\frac{I(\beta()}{I_0}\right)\right)\right) \qquad (8)$$

$K_{SC,forw}$ is a proportionality constant, $I_0$ the intensity of the non-attenuated radiation, and $I(\beta)$ the radiation intensity measured in the fan angle $\beta$ of the detector system. The scattering contributions of all the beams in the fan to all the detector elements are taken into account in the convolutional equation (7) by the convolutional kernel $G(\beta)$;

$$G(\beta) = \left(1 + \left(\frac{\beta}{A \cdot \Delta\beta}\right)^2\right)^{-k} \qquad (9)$$

is usually specified as spacing kernel. A is parameter with which the width can be controlled. It can be determined empirically from image optimizations or from a comparison of stray radiation distributions calculated in the convolutional model and simulated ones. For the function $R(\beta)$ $$R(\beta)=1, \text{ if } \beta\in[=\beta_{max}, \beta_{max}]; 0 \text{ otherwise} \qquad (10)$$

Further information on the above convolutional model for single-row detector systems can be taken from the literature of B. Ohnesorge.

This known model can now be modified within the scope of the invention in order to adapt to multirow or two-dimensional detectors such as shown, for example, in FIG. 2. Equation (7) can easily be expanded because of the rotational symmetry of the differential active cross sections with regard to the fan coordinate $\beta$ and the row coordinate $z_n$ ($z_n=(L/2-n)\Delta z$; $(n=1, \ldots ,L)$). ($\Delta z$ represents the row height). The stray radiation intensity $I_{SC}(\beta, z_n)$ is then given by:

$$I_{SC}(\beta,z_n)=C_M \cdot f(\beta z_{sl}) \cdot (I_{SC,forw}(\beta,z_n) \otimes G(\beta,z_n)) \cdot R(\beta,z_n) \qquad (11)$$

In this case, $C_M$ and $f(\Delta z_{sl})$ have the same meaning as above. $I_{SC,forw}(\beta, z_n)$ is, in turn, the forward scattering radiation intensity calculated in the model of single scattering, with $$I_{SC,forw}(\beta, z_n) = K_{SC,forw} \cdot I(\beta, z_n) \cdot \left(-\ln\left(\frac{I(\beta, z_n)}{I_0}\right)\right) \quad (12)$$

$I(\beta, z_n)$ denotes the radiation intensity measured in the fan angle $\beta$ of the nth detector row. For $R(\beta, z_n)$ that:

$$R(\beta,z_n)=1, \text{ if } \beta\in[-\beta_{max}, \beta_{max}] \text{ and } 1\leq n\leq L;\ 0 \text{ otherwise} \quad (13)$$

The spacing kernel is now:

$$G(\beta, z_n) = \left(1 + \left(\frac{\beta^2 + \left(\frac{z_n}{R_{fd}}\right)^2}{A' \cdot \Delta\beta}\right)\right)^{-k} \quad (14)$$

Here, A' in turn denotes the width parameter, $\beta^2+(z_n/R_{fd})^2$ measures the distance from the detector origin to the detector element in the fan angle $\beta$ of the nth detector row, and $R_{fd}$ denotes the spacing between the focus and detector of the CT scanner.

The stray radiation distribution $I_{SC}(\beta, z_n)$ can be calculated in the previous way for an arbitrary row of the detector matrix 18. It is recommended to calculate it for a middle detector row. The stray radiation distribution thus calculated is then used as reference distribution $I_{Sref}$ for the recursion. The recursion is started in the row from whose measured intensity values the reference distribution was calculated. In the case of a middle detector row, both a recursion to upper detector rows and recursion to lower detector rows are started. If the recursion is interrupted after a fraction of detector rows, a new recursion is begun in a new row, preferably with a new reference distribution that was calculated with the aid of the above convolutional model from the measured values of intensity of this new row. A high quality can be achieved in this way in estimating the accurate stray radiation components.

Although modifications and changes may be suggested by those skilled in the art, it is the invention of the inventor to embody within the patent warranted heron all changes and modifications as reasonably and properly come within the scope of his contribution to the art.

I claim as my invention:

1. A method for correcting for stray radiation in an X-ray computed tomography scanner comprising the steps of:
    irradiating a detector arrangement, composed of a multiplicity of detector elements arranged next to each other in a plurality of adjacent detector rows, with X-rays in a tomography measuring field of a computed tomography scanner;
    from each of said detector elements, obtaining a measured intensity value representing an intensity of X-rays incident thereon;
    obtaining at least one reference distribution of stray radiation intensity in a row direction of said detector arrangement and, for each of said measured intensity values, determining a stray radiation component thereof dependent on said at least one reference distribution; and
    for at least some of said detector rows, correcting the respective measured intensity values of the detector elements thereof as a function of the respective stray radiation components of those measured intensity values by recursion, including the steps of:
        determining the respective stray radiation components of the measured intensity values of the detector elements in a current row in said recursion from the respective measured intensity values of the detector elements of said current detector row, and respective primary radiation components of the respective measured intensity values of detector elements of a preceding detector row in said recursion,
        determining said respective primary radiation components of the measured intensity values of the detector elements of said preceding detector row from measured intensity values of said detector elements of said preceding detector row and the respective stray radiation components of said measured intensity values of the detector elements of said preceding detector row, and
        using intensity values from said reference distribution as the respective stray radiation components of the measured intensity values of detector elements of a first detector row in said recursion.

2. A method as claimed in claim 1 wherein the step of determining said at least one reference distribution comprises:
    disposing a plurality of auxiliary detector elements of said detector arrangement outside of said tomography measuring field; and
    obtaining measured intensity values from said auxiliary detector elements for producing said at least one reference distribution.

3. A method as claimed in claim 2 wherein said detector arrangement comprises a detector matrix having a first detector row and a last detector row, and wherein the step of disposing a plurality of auxiliary detector elements outside of said tomography measuring field comprises disposing said auxiliary detector elements at at least one location selected from the group consisting of above said first detector row and below said last detector row.

4. A method as claimed in claim 3 wherein each of said rows of said detector matrix consists of a number of said detector elements, and wherein the step of disposing a plurality of auxiliary detector elements outside of said tomography measuring field comprises disposing a plurality, which is less than said number, of said auxiliary detector elements at equal spacings in said row direction outside of said tomography measuring field, and obtaining said reference distribution by interpolating the respective measured intensity values from said plurality of auxiliary detector elements.

5. A method as claimed in claim 3 comprising beginning said recursion for respective measured intensity values of detector elements of a detector row of said detector matrix selected from the group consisting of said first detector row and said last detector row.

6. A method as claimed in claim 2 wherein said detector arrangement comprises a detector matrix having a first detector row and a last detector row, and wherein the step of determining said reference distribution comprises the steps of:
    disposing a first plurality of auxiliary detector elements above said first detector row and disposing a second plurality of auxiliary detector elements below said last detector row; and
    obtaining a first reference distribution from respective measured intensity values from said first plurality of auxiliary detector elements and obtaining a second reference distribution from respective measured intensity values from said second plurality of auxiliary detector elements.

7. A method as claimed in claim 1 wherein the step of determining said at least one reference distribution comprises calculating said at least one reference distribution from respective measured intensity values of detector elements in at least one detector row of said detector arrangement.

8. A method as claimed in claim 7 comprising calculating said at least one reference distribution using a mathematical convolution model.

9. A method as claimed in claim 7 wherein said detector arrangement has a middle detector row, and wherein the step of calculating said reference distribution comprises calculating said reference distribution using respective measured intensity values from the detector elements of said middle detector row, and beginning said recursion for detector rows moving outwardly in said detector arrangement from said middle detector row.

10. A method as claimed in claim 1 comprising ending said recursion after proceeding through each detector row in said portion of detector rows, and then beginning a further recursion starting with a subsequent detector row not in said first portion.

11. A method as claimed in claim 10 comprising starting said further recursion using a same reference distribution as was used for said recursion.

12. A method as claimed in claim 10 comprising starting said further recursion using a further reference distribution, different from said reference distribution used for said recursion.

13. A method as claimed in claim 1 wherein said detector arrangement has a column direction perpendicular to said row direction, and comprising the additional steps of:

low-pass filtering said stray radiation components determined from said recursion in at least one direction selected from the group consisting of said column direction and said row direction, to obtain respective filtered stray radiation components for said measured intensity values; and correcting each of said measured intensity values as a function of the filtered stray radiation component thereof.

14. A method as claimed in claim 13 comprising employing a median filter for said low-pass filtering.

15. A method as claimed in claim 1 wherein the step of obtaining at least one reference distribution comprises obtaining two different reference distributions of said stray radiation intensity for each of said measured intensity values, and correcting each of said measured intensity values with an averaged stray radiation component obtained from said two different reference distributions.

16. A method for correcting for stray radiation in an X-ray computed tomography scanner comprising the steps of:

irradiating a detector arrangement, composed of a multiplicity of detector elements arranged next to each other in a plurality of adjacent detector rows, with X-rays in and outside of a tomography measuring field of a computed tomography scanner;

from each of said detector elements, obtaining a measured intensity value representing an intensity of X-rays incident thereon;

obtaining at least one reference distribution of stray radiation intensity in a row direction of said detector arrangement from said measured intensity values from said detector elements outside of said tomography measuring field and, for each of said measured intensity values, determining a stray radiation component thereof dependent on said at least one reference distribution; and for at least some of said detector rows in said tomography measuring field, correcting the respective measured intensity values of the detector elements thereof as a function of the respective stray radiation components of those measured intensity values.

17. A method as claimed in claim 16 comprising, for each measured intensity value, using an intensity value from said reference distribution as said stray radiation component.

18. A method as claimed in claim 17 wherein said detector arrangement comprises a detector matrix having a first detector row and a last detector row, and comprising the step of disposing a plurality of auxiliary detector elements outside of said tomography measuring field at at least one location selected from the group consisting of above said first detector row and below said last detector row.

19. A method as claimed in claim 18 wherein each of said rows of said detector matrix consists of a number of said detector elements, and wherein the step of disposing a plurality of auxiliary detector elements outside of said tomography measuring field comprises disposing a plurality, which is less than said number, of said auxiliary detector elements at equal spacings in said row direction outside of said tomography measuring field, and obtaining said reference distribution by interpolating the respective measured intensity values from said plurality of auxiliary detector elements.

20. A method as claimed in claim 16 wherein said detector arrangement comprises a detector matrix has a first detector row and a last detector row, and wherein the step of determining said reference distribution comprises the steps of:

disposing a first plurality of auxiliary detector elements above said first detector row and disposing a second plurality of auxiliary detector elements below said last detector row; and obtaining a first reference distribution from respective measured intensity values from said first plurality of auxiliary detector elements and obtaining a second reference distribution from respective measured intensity values from said second plurality of auxiliary detector elements.

21. A method as claimed in claim 16 comprising determining said stray radiation component of the respective measured intensity values from detector elements in at least a portion of said detector rows by recursion, including the steps of:

determining the respective stray radiation components of the measured intensity values of the detector elements in a current row in said recursion from the respective measured intensity values of the detector elements of said current detector row, and respective primary radiation components of the respective measured intensity values of detector elements of a preceding detector row in said recursion, determining said respective primary radiation components of the measured intensity values of the detector elements of said preceding detector row from measured intensity values of said detector elements of said preceding detector row and the respective stray radiation components of said measured intensity values of the detector elements of said preceding detector row, and using intensity values from said reference distribution as the respective stray radiation components of the measured intensity values of detector elements of a first detector row in said recursion.

22. A method as claimed in claim 21 wherein said detector arrangement comprises a detector matrix having a first row and a last row, and comprising beginning said recursion for respective measured intensity values of detector elements of a detector row of said detector matrix selected from the group consisting of said first detector row and said last detector row.

23. A method as claimed in claim 21 comprising ending said recursion after proceeding through each detector row in said portion of detector rows, and then beginning a further recursion starting with a subsequent detector row not in said first portion.

24. A method as claimed in claim 21 comprising starting said further recursion using a same reference distribution as was used for said recursion.

25. A method as claimed in claim 24 comprising starting said further recursion using a further reference distribution, different from said reference distribution used for said recursion.

26. A method as claimed in claim 21 wherein said detector arrangement comprises a detector matrix having a column direction perpendicular to said row direction, and comprising the additional steps of:
 low-pass filtering said stray radiation components determined from said recursion in at least one direction selected from the group consisting of said column direction and said row direction, to obtain respective filtered stray radiation components for said measured intensity values; and
 correcting each of said measured intensity values as a function of the filtered stray radiation component thereof.

27. A method as claimed in claim 26 comprising employing a median filter for said low-pass filtering.

28. A method as claimed in claim 16 wherein the step of obtaining at least one reference distribution comprises obtaining two different reference distributions of said stray radiation intensity for each of said measured intensity values from said detector elements outside of said tomography measuring field, and correcting each of said measured intensity values from said detector elements in said tomography measuring field with an averaged stray radiation component obtained from said two different reference distributions.

29. An X-ray computed tomography scanner comprising:
 a detector arrangement including a detector matrix, composed of a multiplicity of detector elements arranged next to each other in a plurality of adjacent detector rows;
 an X-ray source for irradiating said detector arrangement, with X-rays in a tomography measuring field;
 said detector arrangement from each of said detector elements, generating a measured intensity value representing an intensity of X-rays incident thereon;
 an evaluation and reconstruction unit for determining at least one reference distribution of stray radiation intensity in a row direction of said detector matrix and, for each of said measured intensity values, determining a stray radiation component thereof dependent on said at least one reference distribution; and
 said evaluation and reconstruction unit configured to correct for at least some of said detector rows, correcting the respective measured intensity values of the detector elements thereof as a function of the respective stray radiation components of those measured intensity values by recursion, by determining the respective stray radiation components of the measured intensity values of the detector elements in a current row in said recursion from the respective measured intensity values of the detector elements of said current detector row, and respective primary radiation components of the respective measured intensity values of detector elements of a preceding detector row in said recursion, determining said respective primary radiation components of the measured intensity values of the detector elements of said preceding detector row from measured intensity values of said detector elements of said preceding detector row and the respective stray radiation components of said measured intensity values of the detector elements of said preceding detector row, and using intensity values from said reference distribution as the respective stray radiation components of the measured intensity values of detector elements of a first detector row in said recursion.

30. A computed tomography scanner as claimed in claim 29 wherein said detector arrangement includes a plurality of auxiliary detector elements disposed outside of said tomography measuring field, and wherein said evaluation and reconstruction unit determines said reference distribution from respective measured intensity values from said auxiliary detector elements.

31. A computed tomography scanner as claimed in claim 30 wherein said detector matrix has a first detector row and a last detector row, and wherein said auxiliary detector elements are disposed at equidistant spacings in said row direction at at least one location selected from the group consisting of above said first detector row and below said last detector row.

32. A computed tomography scanner as claimed in claim 31 wherein each row of said detector matrix consists of a number of said detector elements, and wherein said plurality of auxiliary detector elements is smaller than said number.

33. A computed tomography scanner as claimed in claim 32 wherein each of said rows of detector elements in said detector matrix comprises a number of detector elements, and wherein said detector elements outside of said tomography measuring field comprise a plurality which is less than said number.

34. An X-ray computed tomography scanner comprising:
 a detector arrangement, composed of a multiplicity of detector elements arranged next to each other in a plurality of adjacent detector rows;
 an X-ray source for irradiating said detector arrangement with X-rays in a tomography measuring field, said detector arrangement including detector elements in said tomography measuring field and detector elements outside of said tomography measuring field;
 said detector arrangement, from each of said detector elements, generating a measured intensity value representing an intensity of X-rays incident thereon;
 an evaluation and reconstruction unit for determining at least one reference distribution of stray radiation intensity in a row direction of said detector arrangement from said measured intensity values for said detector elements outside of said tomography measuring field and, for each of said measured intensity values from said detector elements in said tomography measuring filed, determining a stray radiation component thereof dependent on said at least one reference distribution; and
 for at least some of said detector rows in said tomography measuring field, correcting the respective measured intensity values of the detector elements thereof as a function of the respective stray radiation components.

35. A computed tomography scanner as claimed in claim 34 wherein said detector arrangement includes a detector matrix having a first detector row and a last detector row, and wherein said detector elements disposed outside of said tomography measuring field are disposed at equidistant spacings in said row direction at at least one location selected from the group consisting of above said first detector row and below said last detector row.

* * * * *